United States Patent [19]

Samreth et al.

[11] Patent Number: 5,100,913

[45] Date of Patent: Mar. 31, 1992

[54] NOVEL SULFONYLPHENYL-β-D-THIOXYLOSIDES, THEIR METHOD OF PREPARATION AND THEIR USE IN THERAPEUTICS

[75] Inventors: Soth Samreth, Longvic; Patrice Renaut, Hauteville les Dijon; Jerzy Bajgrowicz, Dijon; Jean Millet, Corcelles les Citeaux, all of France

[73] Assignee: Fournier Industrie et Sante, Paris, France

[21] Appl. No.: 674,131

[22] Filed: Mar. 25, 1991

[30] Foreign Application Priority Data

Apr. 2, 1990 [FR] France ................... 90 04173

[51] Int. Cl.$^5$ .............. A61K 31/38; C07D 335/02
[52] U.S. Cl. .................. 514/432; 514/24; 514/326; 514/231.5; 514/822; 549/28; 546/207; 544/196; 536/4.1; 536/18.4
[58] Field of Search ............ 549/28; 514/432, 24, 514/326, 231.5, 822; 536/4.1, 18.4; 546/207; 544/146

[56] References Cited

U.S. PATENT DOCUMENTS 4,877,808  10/1989  Samreth et al. ................ 314/432

Primary Examiner—Glennon H. Hollrah
Assistant Examiner—Mark W. Russell

Attorney, Agent, or Firm—Fleit, Jacobson, Cohn, Price, Holman & Stern

[57] ABSTRACT

The present invention relates, by way of novel industrial products, to the sulfonylphenyl-β-D-thioxyloside compounds of the formula

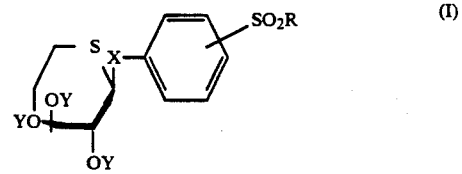

in which:
  X is a sulfur atom or an oxygen atom;
  R is a $C_1$-$C_4$ alkyl group, a substituted amino group $NR_1R_2$ (where $R_1$ and $R_2$, which are identical or different, are each a $C_1$-$C_4$ alkyl group, it being possible for $R_1$ and $R_2$, taken together, to form a piperidinyl or morpholinyl group with the nitrogen atom to which they are bonded) or a phenyl group which is unsubstituted or substituted in the para position by a cyano group or by a halogen atom; and
  Y is the hydrogen atom or an aliphatic acyl group.

These compounds are useful in therapeutics, especially as venous antithrombotics.

8 Claims, No Drawings

NOVEL SULFONYLPHENYL-β-D-THIOXYLOSIDES, THEIR METHOD OF PREPARATION AND THEIR USE IN THERAPEUTICS

The present invention relates, by way of novel industrial products, to the sulfonylphenyl-β-D-thioxyloside compounds of formula I below. It further relates to their method of preparation and to their use in therapeutics as antithrombotics, especially venous antithrombotics.

EP-B-0 051 023 has already disclosed benzoylphenyloside and α-hydroxybenzylphenyloside derivatives as anti-ulcer agents, platelet aggregation inhibitors, antithrombotics and cerebral oxygenators.

Also, EP-A-0 133 103 has disclosed benzylphenylosides which are useful as hypocholesterolemics and hypolipidemics, some of these compounds, in particular the product of Example 1, having antithrombotic effects as well.

Finally, EP-A-0 290 321 has disclosed benzoylphenylthioxylose, α-hydroxybenzylphenylthioxylose and benzylphenylthioxylose derivatives as antithrombotics.

It has now just been found that the sulfonylphenyl-B-D-thioxyloside compounds according to the invention, which are structurally different from the known products of the prior art, are useful in the treatment and prevention of diseases associated with circulatory disorders, and especially as venous antithrombotics.

The novel products according to the invention are selected from the group consisting of the sulfonylphenyl-β-D-thioxylosides of the formula

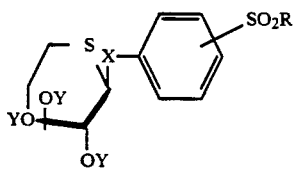

in which:

X is a sulfur atom or an oxygen atom;

R is a $C_1$–$C_4$ alkyl group, a substituted amino group $NR_1R_2$ (where $R_1$ and $R_2$, which are identical or different, are each a $C_1$–$C_4$ alkyl group, it being possible for $R_1$ and $R_2$, taken together, to form a piperidinyl or morpholinyl group with the nitrogen atom to which they are bonded) or a phenyl group which is unsubstituted or substituted in the para position by a cyano group or by a halogen atom; and Y is the hydrogen atom or an aliphatic acyl group.

Among the aliphatic acyl groups which are suitable according to the invention, there may be mentioned those which contain a total of 2 to 5 carbon atoms, the preferred aliphatic acyl group being $CH_3CO$.

$C_1$–$C_4$ alkyl group is understood here as meaning a linear or branched hydrocarbon radical containing 1 to 4 carbon atoms, the preferred alkyl group being the methyl group.

Halogen atom is understood here as meaning a chlorine, fluorine or bromine atom, the preferred halogen atom being the fluorine atom.

According to the invention, the preferred compounds of formula I are those in which X is the sulfur atom.

The compounds of formula I and the corresponding acylated compounds can be prepared by a glycosylation reaction which comprises

in which X and R are as defined above, with a thioxylose derivative selected from the group consisting of (i) the acylthioxylosyl halides of the formula

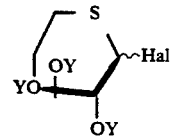

(ii) the peracylated thioxyloses of the formula

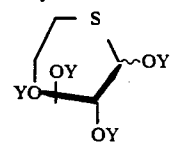

and (iii) the acylthioxylosyl trichloroacetimidates of the formula

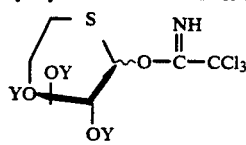

in which Hal is a halogen atom such as Cl or Br (the bromine atom being the preferred halogen atom here) and Y is an acyl group, especially an aliphatic acyl group containing a total of 2 to 5 carbon atoms and preferably the acetyl group, in an inert solvent, at a rate of 1 mol of II to about 0.6 to 1.2 mol of compound III, IV or V, especially in the presence of an acid acceptor and/or a Lewis acid, and (ii) if necessary, subjecting the resulting compound of formula I in which Y is a $C_2$–$C_5$ acyl group to a deacylation reaction at a temperature of between 0° C. and the reflux temperature of the reaction medium, in a $C_1$–$C_4$ lower alcohol (preferably methanol), in the presence of a metal alcoholate (preferably magnesium methylate or sodium methylate), to give a compound of formula I in which Y is H.

Compounds III, IV and V can be in the α or β configuration or in the form of an anomeric mixture of both configurations.

The glycosylation reactions of the compounds of formula II were carried out either starting from compound III in the presence of a catalyst such as salts or oxides of silver, mercury or zinc, or starting from compound V in the presence of a Lewis acid, especially boron trifluoride etherate or zinc chloride, or starting from compound IV in the presence of a Lewis acid.

According to one preferred mode of carrying out the invention, it is recommended to condense 1 mol of the compound of formula II with about 1.1 to 1.2 mol of acylthioxylosyl halide III in an inert solvent selected from polar or apolar solvents (such as, for example, dimethylformamide, tetrahydrofuran, dioxane, acetonitrile, nitromethane, benzene, toluene, xylenes and mixtures thereof), in the presence of mercuric cyanide.

It is advantageous to use 2,3,4-tri-O-acetyl-5-thio-α-D-xylopyranosyl bromide in a benzene/nitromethane mixture (1/1 v/v), in the presence of 1.1 to 1.3 mol of mercuric cyanide, at a temperature of between 0° C. and the reflux temperature of the reaction medium, preferably at about 40°-50° C., for 1 to 4 hours, preferably for about 2 hours.

According to a second preferred mode of carrying out the invention, it is recommended to condense 1 mol of the compound of formula II with about 1.1 to 1.2 mol of acylthioxylosyl halide III in an inert solvent (such as, for example, methylene chloride or acetonitrile), in the presence of silver imidazolate and zinc chloride.

It will be advantageous to use 2,3,4-tri-O-acetyl-5-thio-D-xylopyranosyl bromide in methylene chloride or a methylene chloride/acetonitrile mixture, in the presence of 1.5 to 1.7 mol of silver imidazolate and 2 to 2.2 mol of zinc chloride, at a temperature of between 0° C. and the reflux temperature of the reaction medium, preferably at about 40°-60° C., for 24 to 48 hours.

According to a third preferred mode of carrying out the invention, it is recommended to condense 1 mol of the compound of formula II with about 0.6 to 1 mol of acylthioxylosyl halide III in an inert solvent (such as, for example, toluene and/or acetonitrile), in the presence of zinc oxide.

It will be advantageous to use 2,3,4-tri-O-acetyl-5-thio-D-xylopyranosyl bromide in a toluene/acetonitrile mixture, in the presence of 0.5 to 1.2 mol of zinc oxide, at a temperature between room temperature and the reflux temperature of the reaction medium, preferably at about 40°-60° C., for 18 to 48 hours.

According to a fourth preferred mode of carrying out the invention, it is recommended to condense 1 mol of the compound of formula II with about 1.1 to 1.3 mol of acylthioxylosyl trichloroacetimidate in an inert solvent (such as, for example, methylene chloride or acetonitrile), in the presence of boron trifluoride etherate or zinc chloride.

It will be advantageous to use 2,3,4-tri-O-acetyl-5-thio-α-D-xylopyranosyl trichloroacetimidate in methylene chloride, in the presence of a solution of 0.1 to 0.4 mol of boron trifluoride etherate in methylene chloride or acetonitrile, or in the presence of zinc chloride, at a temperature of between −40° C. and room temperature (15°-25° C.), preferably at about −20° C. to 0° C., for 1 to 5 hours.

In all cases, the glycosylation reaction yields a mixture of the isomers of α and β configuration in variable proportions.

The isomer of β configuration is isolated by the methods known to those skilled in the art, such as, for example, fractional crystallization or chromatography, especially flash chromatography [i.e. chromatography on a silica column, under pressure, according to the technique described by W. C. STILL et al. in J. Org. Chem. (1978) 42 (n° 14) 2923].

Where appropriate, the derivatives obtained are subjected to deacylation, and more particularly to deacetylation, which is carried out at a temperature of between 0° C. and the reflux temperature of the reaction medium, in a $C_1$-$C_4$ lower alcohol, in the presence of the corresponding metal alcoholate. Preferably, methanol will be chosen as the lower alcohol and sodium or magnesium methylate as the metal alcoholate.

If desired, the deacylation reaction can be carried out after glycosylation without isolation of the acylated intermediate formed.

It is also possible to carry out the deacylation reaction enzymatically, for example using pork liver esterase.

To obtain the intermediates of formula II in which X=S, it is recommended to (i) condense dimethylaminothiocarbamoyl chloride of the formula

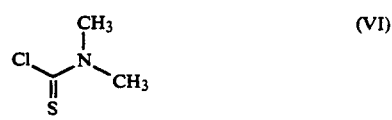

in a strong basic medium with a compound of the formula

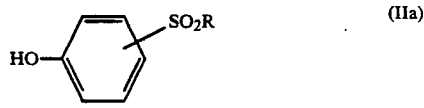

in which R is as defined above, to give a compound of the formula

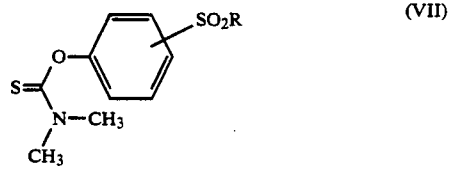

in which R is as defined above, (ii) subject the resulting compound of formula VII to a Newmann rearrangement (J. Org. Chem. (1966) 31, p. 3980), by heating, to give a compound of the formula (VIII)

in which R is as defined above, and (iii) treat the resulting compound of formula VIII with a metal alcoholate, preferably sodium or magnesium methylate, in a $C_1$-$C_4$ lower alcohol, preferably methanol, dimethylformamide or dioxane, to give a compound of formula II in which X=S.

The intermediates of formula II in which X=S can also be obtained by the nucleophilic substitution of an appropriate halogenobenzene compound using the method described by L. TESTAFERRI in Tetrahedron Letters, vol. 21, p. 3099–3100 (1980).

Some of the intermediates of formula II in which X=S are novel compounds.

The compounds of the formula

The compounds of the formula

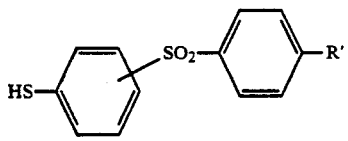

in which R' is a fluorine atom, a bromine atom or a cyano group therefore form one of the subjects of the invention.

According to the invention, a therapeutic composition is proposed which contains, in association with a physiologically acceptable excipient, at least one compound selected from the group consisting of the products of formula I. Of course, in such a composition, the active ingredient is present in a therapeutically effective amount.

The compounds of formula I are useful in therapeutics as antithrombotics. They are particularly useful in the prevention and treatment of disorders of the venous circulation.

According to the invention, it is recommended to use a substance belonging to the group consisting of the compounds of formula I in order to obtain an antithrombotic drug for use in therapeutics to combat disorders of the venous circulation.

Further characteristics and advantages of the invention will be understood more clearly from the following description of Preparatory Examples, which in no way imply a limitation but are given by way of illustration, and results of pharmacological tests.

In the Preparatory Examples which follow, the α or β configuration has been specified in the compound names in cases where said configuration was determined. Where the configuration is not indicated, this means that the corresponding product is an anomeric mixture of the α and β configurations in proportions which were not determined.

PREPARATION I

I a) Preparation of 4-(phenylsulfonyl)benzenethiol 1.25 g of sodium thiomethylate are added under a nitrogen atmosphere to a solution of 15 g (0.0593 mol) of 1-chloro-4-(phenylsulfonyl)benzene in 150 ml of hexamethylphosphoramide. The mixture obtained is heated for 4 hours at 100° C. and then cooled and hydrolyzed in an ice/water mixture. The reaction medium obtained is extracted with ethyl acetate and the aqueous phase obtained is then poured into a 4 N solution of hydrochloric acid at 0° C. The product formed precipitates. After filtration, washing with water until the pH of the washings is neutral, and drying, 13.44 g (yield: 90.5%) of the expected product are obtained. M.p.=117° C.

I b) Preparation of 4-(phenylsulfonyl)phenyl 2,3,4-tri-O-acetyl-1,5-dithio-β-D-xylopyranoside (Example 1)

10.6 g of mercuric cyanide (Hg(CN)$_2$) are added under nitrogen to a solution of 10 g (0.0399 mol) of 1-mercapto-4-(phenylsulfonyl)benzene in 300 ml of a toluene/nitromethane mixture (1/1 v/v) and the mixture obtained is then stirred for 1 hour at 40°-45° C. Precipitation is observed. 17.7 g (0.0498 mol) of 2,3,4-tri-O-acetyl-1-bromo-5-thio-β-D-xylopyranoside are then added to the mixture. After stirring for 3.5 h at 40°-45° C., the reaction medium becomes clear. The organic phase obtained after cooling is washed successively with a 1 N solution of hydrochloric acid at 0° C., a 1 N solution of sodium hydroxide at 0° C., water and then a saturated solution of sodium chloride. After evaporation of the solvents, 24 g of a yellow foam are obtained which crystallizes on the addition of ether. 8.6 g of the expected product (yield: 41%) are finally obtained.

M.p.=159° C.
$[\alpha]_D^{23}$= +58.2 (c=0.5; CHCl$_3$).

I c) Preparation of 4-(phenylsulfonyl)phenyl 1,5-dithio-β-D-xylopyranoside (Example 2)

A solution of 0.35 cm$^3$ of sodium methylate in methanol (3.5 molar) is added to a suspension of 6.5 g of 4-(phenylsulfonyl)phenyl 2,3,4-tri-O-acetyl-1,5-dithio-β-D-xylopyranoside in 150 ml of methanol. The mixture obtained is stirred at room temperature for 1.5 h under nitrogen and 250 cm$^3$ of tetrahydrofuran are then added. A clear solution is obtained, after which Amberlite ® IR 120 H+ resin is added to pH 6. The mixture is filtered and the solvents are evaporated off under reduced pressure. After recrystallization from a methanol/water mixture (50/50 v/v), followed by dissolution in an ethanol/water mixture (50/50 v/v) and lyophilization, 3.3 g of the expected product (yield: 67%) are obtained.

M.p.=melting range from 85° C. to 97° C.
$[\alpha]_D^{23}$= +44.8. (c=0.42; dimethyl sulfoxide)

PREPARATION II

II a) Preparation of 1-bromo-2-(methylsulfonyl)benzene

A solution of 5 g (0.0246 mol) of 1-bromo-2-(methylthio)benzene in 10 ml of methanol is cooled to 0° C. under a nitrogen atmosphere and 1.27 g of 50% 3-chloroperoxybenzoic acid (MCPBA) are then added. Stirring at 0° C. is maintained for 45 minutes, 6 g of potassium fluoride are then added and hydrolysis is continued for 12 hours. The medium obtained is filtered on Célite ® and the product obtained after evaporation of the solvents is then purified by flash chromatography using a toluene/ethyl acetate mixture (95/5 v/v) as the eluent. 5.63 g (yield: 97%) of the expected product are obtained.

M.p.=98° C.

II b) Preparation of 2-(methylsulfonyl)benzenethiol

The expected product is obtained by following a procedure analogous to Preparation I a).
M.p.=57° C.

II c) Preparation of 2-(methylsulfonyl)phenyl 2,3,4-tri-O-acetyl-1,5-dithio-β-D-xylopyranoside (Example 3)

8.43 g (0.0251 mol) of 1-bromo-2,3,4-tri-O-acetyl-1,5-thio-β-D-xylopyranoside are added to a mixture of 4.3 g (0.0228 mol) of 1-mercapto-2-(methylsulfonyl)benzene and 1.95 g of zinc oxide in 90 ml of toluene/acetonitrile (1/1 v/v) and the mixture obtained is heated at 45° C. for 2 hours. The medium obtained is filtered on Celite ® and the organic phase is then washed with a 1 N solution of HCl, a 1 N solution of sodium hydroxide and then water until the pH of the washings is neutral. After evaporation of the solvents under reduced pressure, an oil is obtained which crystallizes on the addition of ether. The 5.33 g of crystalline product obtained are then purified by flash chromatography using a toluene- /ethyl acetate mixture (8/2 v/v) as the eluent. 4.35 g (yield: 41%) of the expected product are obtained.
M.p.=209° C.
$[\alpha]_D^{20} = +38.4$. (c=0.5; CHCl$_3$).

II d) Preparation of 2-(methylsulfonyl)phenyl 1.5-dithio-β-D-xylopyranoside (Example 4)

The expected product is obtained by following a procedure analogous to Preparation I c).
M.p.=139° C.,
$[\alpha]_D^{20} = +38.8$. (c=0.5; CH$_3$OH).

PREPARATION III

III a) Preparation of 4-(methylsulfonyl)phenyl 2,3,4-tri-O-acetyl-1,5-dithio-β-D-xylopyranoside (Example 5)

By following a procedure analogous to Preparation II c), a colorless oil is obtained which crystallizes from ether.
M.p.=105°-110° C.
$[\alpha]_D^{20} = +71°$ (c=0.5; CHCl$_3$).

III b) Preparation of 4-(methylsulfonyl)phenyl 1,5-dithio-β-D-xylopyranoside (Example 6)

By following a procedure analogous to Preparation I c), the expected product is obtained after recrystallization from a methanol/ethanol mixture.
M.p.>250° C.
$[\alpha]_D^{20} = +19.2$. (c=0.5; CH$_2$Cl$_2$/CH$_3$OH (1/1 v/v)).

PREPARATION IV

IV a) Preparation of 4-(methylsulfonyl)phenyl 2,3,4-tri-O-acetyl-5-thio-β-D-xylopyranoside (Example 7)

A mixture of 2 g (0.012 mol) of 1-hydroxy-4(methylsulfonyl)benzene, 3.17 g of zinc chloride (ZnCl$_2$), 4.5 g (0.013 mol) of 1-bromo-2,3,4-tri-O-acetyl-5-thio-β-D-xylopyranoside and 3.1 g (0.0177 mol) of silver imidazolate (C$_3$H$_3$AgN$_2$) in 70 ml of methylene chloride is heated for 20 hours at 50° C. After cooling, the reaction medium is filtered, the organic phase obtained is then washed successively with a 1 N solution of hydrochloric acid, water and a 1 N solution of sodium hydroxide and the solvent is then evaporated off under reduced pressure. 1.1 g of the expected product (yield: 21.2%) are obtained after purification by flash chromatography using a toluene/ethyl acetate mixture (3/1 v/v) as the eluent, followed by precipitation in ethyl ether.
M.p.=168° C.
$[\alpha]_D^{22} = -75°$ (c=0.6; CHCl$_3$).

IV b) Preparation of 4-(methylsulfonyl)phenyl 5-thio-β-D-xylpyranoside (Example 8)

The expected product is obtained, after lyophilization, by following a procedure analogous to Preparation I c).
M.p.=180° C.
$[\alpha]_D^{22} = -77.2$ (c=0.5; CH$_3$OH).

PREPARATION V

V a) Preparation of 4-(ethylsulfonyl)benzenethiol

The expected product is obtained in the form of an oil by following a procedure analogous to Preparation I a).
$n_D^{24} = 1.5891$.

V b) Preparation of 4-(ethylsulfonyl)phenyl 2,3,4-tri-O-acetyl-1,5-dithio-β-D-xylpyranoside (Example 9)

The expected product is obtained by following a procedure analogous to Preparation I b).
M.p.=136°-137° C.
$[\alpha]_D^{23} = +36.7$ (c=0.45; CHCl$_3$)

V c) Preparation of 4-(ethylsulfonyl)phenyl 1,5dithio-β-D-xylopyranoside (Example 10)

The expected product is obtained by following a procedure analogous to Preparation I c).
M.p.=130°-135° C.
$[\alpha]_D^{23} = +26.8°$ (c=0.485; methanol)

PREPARATION VI

VI a) Preparation of 4-(methylsulfonyl)phenyl 2,3,4-tri-O-acetyl-1,5-dithio-β-D-xylopyranoside (Example 11)

The expected product is obtained by following a procedure analogous to Preparation II c).
M.p.=147°-150° C.
$[\alpha]_D^{21} = -10.5°$ (c=0.3; CHCl$_3$).

VI b) Preparation of 4-(methylsulfonyl)phenyl 1.5-dithio-β-D-xylopyranoside (Example 12)

The expected product is obtained by following a procedure analogous to Preparation I c).
M.p.=169°-172° C.
$[\alpha]_D^{22} = -12.2°$ (c=0.45; dimethyl sulfoxide).

PREPARATION VII

VII a) Preparation of 4-[(4-fluorophenyl)sulfonyl]benzenethiol

A solution of sodium nitrite (302 mg in 1 ml of water) is added to a suspension of 1 g (0.00398 mol) of 4-[(4-fluorophenyl)sulfonyl]benzeneamine in a solution of hydrochloric acid (1.68 ml of concentrated hydrochloric acid in 5 ml of water) at 5° C. After stirring for 5 minutes, this solution is added dropwise to a solution of 2.47 g of potassium ethylxanthate in 5 ml of water at 70° C. The reaction mixture is diluted with ethyl acetate. The organic phase is washed with a 1 N solution of sodium hydroxide and a saturated solution of sodium chloride and then dried over magnesium sulfate. After evaporation of the solvents, the residue is taken up in 15 ml of ethanol. 1.47 g of potassium hydroxide are added and the reaction mixture is heated at 45° C. for 10 minutes. It is then poured into iced water and partially purified by extraction with ethyl acetate. The aqueous phase, cooled with ice, is rendered acidic by the addition of concentrated hydrochloric acid and is then extracted with ethyl acetate. The organic phase is dried over magnesium sulfate and the solvents are evaporated off to dryness. 640 mg (yield: 60%) of the expected product are thus obtained.
M.p.=116° C.

VII b) Preparation of 4-[(4-fluorophenyl)sulfonylphenyl 2,3,4-tri-O-acetyl-1,5-dithio-β-D-xylopyranoside (Example 13)

The expected product is obtained by following a procedure analogous to Preparation II c).
M.p.=80° C.
$[\alpha]_D^{21} = +48.4$ (c=0.5; CHCl$_3$)

VII c) Preparation of 4-[(4-fluorophenyl)sulfonyl]phenyl 1,5-dithio-β-D-xylpyranoside (Example 14)

The expected product is obtained by following a procedure analogous to Preparation I c).
M.p. = 136°–138° C.
$[\alpha]_D^{21} = +40$ (c = 0.5; dimethyl sulfoxide).

PREPARATION VIII

VIII a) Preparation of 4-[(4-methoxyphenyl)sulfonyl]benzonitrile 6 g (0.0248 mol) of 4-[(4-methoxyphenyl)thio]benzonitrile and then 18.45 g of magnesium monoperoxyphthalate hexahydrate are added to a mixture of 120 ml of ethanol and 12 ml of water. The reaction medium is kept at 40° C. for 20 minutes. After hydrolysis in iced water, the solution is filtered and the white solid is washed with water. 5.2 g (yield: 77%) of the expected product are thus obtained.
M.p. = 135° C.

VIII b) Preparation of 4-[(4-hydroxyphenyl)sulfonyl]benzonitrile

A mixture of 5.12 g (0.0187 mol) of 4-[(4-methoxyphenyl)sulfonyl]benzonitrile and 21.6 g of pyridinium hydrochloride is kept at 200° C. for 2 hours. After cooling, the reaction medium is hydrolyzed in a 1 N solution of hydrochloric acid. The precipitate formed is filtered off and rinsed with a 1 N solution of hydrochloric acid and then with water until the pH of the washings is neutral. 4.5 g (yield: 99%) of the expected product are thus obtained in the form of a gray solid.
M.p. = 177° C.

VIII c) Preparation of O-[4-((4-cyanophenyl)sulfonyl)phenyl] dimethylthiocarbamate 2.36 g (0.0097 mol) of 4-[(4-hydroxyphenyl)sulfonyl]benzonitrile are added to a solution of 570 mg of potassium hydroxide in 35 ml of water. The solution is kept at room temperature for 15 minutes. After cooling to 0° C., a solution of 1.38 g of N,N-dimethylthiocarbamoyl chloride in 35 ml of acetone is added dropwise. After 4 hours, the reaction mixture is hydrolyzed in a 1 N solution of hydrochloric acid. The solution is extracted with ethyl acetate. The organic phase is washed with water until the pH of the washings is neutral, dried over magnesium sulfate and concentrated to dryness. 3 g (yield: 100%) of the expected product are thus obtained.
M.p. = 158°–167° C.

VIII d) Preparation of S-[4-((4-cyanophenyl)sulfonyl)phenyl]dimethylthiocarbamate 3 g (0.0096 mol) of O-[4-((4-cyanophenyl)sulfonyl)phenyl] dimethylthiocarbamate are kept at 200° C. for 30 minutes. After chromatography on silica gel using a toluene/ethyl acetate mixture (8/2 v/v) as the eluent, 2.29 g (yield: 76%) of the expected product are obtained.
M.p. = 140° C.

VIII e) Preparation of 4-(4-mercaptophenyl)sulfonyl]benzonitrile 4.1 ml of sodium methylate (8% of Na (w/v) in methanol) are added to a solution of 2.25 g (0.0075 mol) of S-[4-((4-cyanophenyl)sulfonyl)phenyl] dimethylthiocarbamate in 45 ml of N,N-dimethylformamide at 0° C. The reaction mixture is then hydrolyzed in an iced 1 N solution of hydrochloric acid. After filtration, the precipitate formed is washed with water and then dried. 1.54 g (yield: 78%) of the expected product are thus obtained.
M.p. = 166° C.

VIII f) Preparation of 4-((4-cyanophenyl)sulfonyl)phenyl 2,3,4-tri-O-acetyl-1,5-dithio-β-D-xylpyranoside (Example 15)

The expected product is obtained by following a procedure analogous to Preparation I b).
M.p. = 194°–195° C.
$[\alpha]_D^{20} = +51°$ (c = 0.5; CHCl$_3$).

VIII g) Preparation of 4-((4-cyanophenyl)sulfonyl)phenyl 1,5-dithio-β-D-xylopyranoside (Example 16)

The expected product is obtained by following a procedure analogous to Preparation I c).
M.p. = 175°–183° C.
$[\alpha]_D^{20} = +58.6°$ (c = 0.5; dimethyl sulfoxide).

PREPARATION IX

IX a) Preparation of 4-(N,N-dimethylsulfonamidyl)phenyl 2,3,4-tri-O-acetyl-1,5-dithio-β-D-xylpyranoside (Example 17)

The expected product is obtained by following a procedure analogous to Preparation I b).
M.p. = 120° C.
$[\alpha]_D^{20} = +35.4$ (c = 0.56; CHCl$_3$)

IX b) Preparation of 4-(N,N-dimethylsulfonamidyl)phenyl 1.5-dithio-β-D-xylopyranoside (Example 18)

The expected product is obtained by following a procedure analogous to Preparation I c).
M.p. = 208°–213° C.
$[\alpha]_D^{24} = +21.4$ (c = 0.42; dimethyl sulfoxide)

PREPARATION X

X a) Preparation of 4-(N,N-dimethylsulfonamidyl)phenyl 2,3,4-tri-O-acetyl-5-thio-β-D-xylpyranoside (Example 19)

The expected product is obtained by following a procedure analogous to Preparation IV a).
M.p. = 85° C. then 164°–167° C. (double melting point) $[\alpha]_D^{25} = -57.6$ (c = 0.33; CHCl$_3$).

X b) Preparation of 4-(N,N-dimethylsulfonamidyl)phenyl 5-thio-β-D-xylpyranoside (Example 20)

The expected product is obtained by following a procedure analogous to Preparation I c).
M.p. = 205° C.
$[\alpha]_D^{21} = -70.4$ (c = 0.27; methanol).

PREPARATION XI

XI a) Preparation of 4-mercapto-N-(piperidin-1-yl)benzenesulfonamide

The expected product is obtained by following a procedure analogous to Preparation I a).

M.p.=93° C.

XI b) Preparation of 4-(N-(piperidin-1-yl)sulfonamidyl)phenyl 2,3,4-tri-O-acetyl-1,5-dithio-β-D-xylopyranoside (Example 21)

The expected product is obtained by following a procedure analogous to Preparation I b).
M.p.=175°-180° C.
$[\alpha]_D^{22} = +39.8°$ (c=0.425; CHCl$_3$).

XI c) Preparation of 4-(N-(piperidin-1-yl)sulfonamidyl)phenyl 1,5-dithio-β-D-xylpyranoside (Example 22)

The expected product is obtained by following a procedure analogous to Preparation I c).
M.p.=145°-149° C.
$[\alpha]_D^{22} = +23.8°$ (c=0.21; methanol).

PREPARATION XII

XII a) Preparation of 4-mercapto-N-(morpholin-1-yl)benzenesulfonamide

The expected product is obtained by following a procedure analogous to Preparation I a).
M.p.=128° C.

XII b) Preparation of 4-(N-(morpholin-1-yl)sulfonamidyl)phenyl 2,3,4-tri-O-acetyl-1,5-dithio-β-D-xylopyranoside (Example 23)

The expected product is obtained by following a procedure analogous to Preparation I b).
M.p.=120°-123° C.
$[\alpha]_D^{22} = +39°$ (c=0.39; CHCl$_3$)

XII c) Preparation of 4-(N-(morpholin-1-yl)sulfonamidyl)phenyl 1,5-dithio-β-D-xylopyranoside (Example 24)

The expected product is obtained by following a procedure analogous to Preparation I c).
M.p.=90°-105° C.
$[\alpha]_D^{22} = +20.4°$ (c=0.56; dimethyl sulfoxide)

The compounds according to the invention have been collated in Table I below, without implying a limitation.

The antithrombotic activity of the products according to the invention was demonstrated using the following operating protocol for venous thrombosis:

A venous stasis under hypercoagulation is produced according to the technique described by WESSLER et al. (J. Applied Physiol. 1959, p. 943-946). As in the technique described by J. HAUPMAN et al. (Thrombosis and Haemostasis 43(2), 1980, p. 118), the hypercoagulant used is a solution of activated factor X (Xa) supplied by Flow Laboratories (71 Knat per 12.5 ml of isotonic solution).

The study is performed on unfasted male Wistar rats weighing 250 to 280 g, divided into groups of 10 animals each. The test products are administered orally as a suspension in PEG 400. A thrombosis is induced 4 hours after this treatment and the thrombus formed is removed and weighed.

The results obtained at a dose of 3 mg/kg, administered orally, have been collated in Table I. The results obtained with the known products of the afore-mentioned prior art have also been collated in this Table.

TABLE I

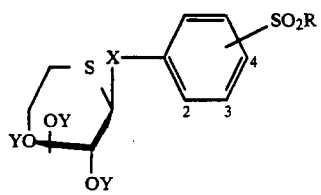

(I)

| Example | X | Position of SO$_2$R | R | Y | % inhibition at 3 mg/kg |
|---|---|---|---|---|---|
| 1 | S | 4 | —C$_6$H$_5$ | —COCH$_3$ | 20 |
| 2 | S | 4 | —C$_6$H$_5$ | —H | 49 |
| 3 | S | 2 | —CH$_3$ | —COCH$_3$ | 29 |
| 4 | S | 2 | —CH$_3$ | —H | 26 |
| 5 | S | 4 | —CH$_3$ | —COCH$_3$ | — |
| 6 | S | 4 | —CH$_3$ | —H | 61 |
| 7 | O | 4 | —CH$_3$ | —COCH$_3$ | — |
| 8 | O | 4 | —CH$_3$ | —H | 30 |
| 9 | S | 4 | —CH$_2$—CH$_3$ | —COCH$_3$ | 31 |
| 10 | S | 4 | —CH$_2$—CH$_3$ | —H | 31 |
| 11 | S | 3 | —CH$_3$ | —COCH$_3$ | — |
| 12 | S | 3 | —CH$_3$ | —H | 43 |
| 13 | S | 4 | 4-F—C$_6$H$_5$ | —COCH$_3$ | 58 |
| 14 | S | 4 | 4-F—C$_6$H$_5$ | —H | 61 |
| 15 | S | 4 | 4-CN—C$_6$H$_5$ | —COCH$_3$ | — |
| 16 | S | 4 | 4-CN—C$_6$H$_5$ | —H | 66 |
| 17 | S | 4 | —N(CH$_3$)$_2$ | —COCH$_3$ | 56 |
| 18 | S | 4 | —N(CH$_3$)$_2$ | —H | 46 |
| 19 | O | 4 | —N(CH$_3$)$_2$ | —COCH$_3$ | 23 |
| 20 | O | 4 | —N(CH$_3$)$_2$ | —H | 58 |
| 21 | S | 4 | 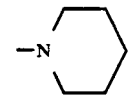 | —COCH$_3$ | — |

TABLE I-continued

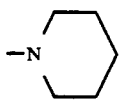

| Example | X | Position of SO₂R | R | Y | % inhibition at 3 mg/kg |
|---|---|---|---|---|---|
| 22 | S | 4 | —N(piperidinyl) | —H | 47 |
| 23 | S | 4 | —N(morpholinyl) | —COCH₃ | — |
| 24 | S | 4 | —N(morpholinyl) | —H | — |
| A | | | Comparative product described in Example 1 of EP-A-0 133 103 | | 14(1) |
| B | | | Comparative product described in Example 97 of EP-B-0 051 023 | | 5.5(1) |
| C | | | Comparative product described in Example 3 of EP-A-0 290 321 | | 20(2) |

Notes:
(1) product tested at 12.5 mg/kg, administered orally
(2) product tested at 3 mg/kg, administered orally

What is claimed is:

1. An oside compound selected from the group consisting of the sulfonylphenyl-β-D-thioxylosides of the formula

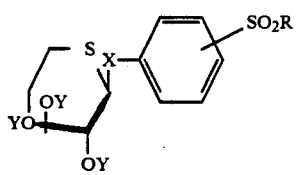

in which:

X is a sulfur atom or an oxygen atom;

R is a $C_1$-$C_4$ alkyl group, a substituted amino group $NR_1R_2$ (where $R_1$ and $R_2$, which are identical or different, are each a $C_1$-$C_4$ alkyl group, it being possible for $R_1$ and $R_2$, taken together, to form a piperidinyl or morpholinyl group with the nitrogen atom to which they are bonded) or a phenyl group which is unsubstituted or substituted in the para position by a cyano group or by a halogen atom; and Y is the hydrogen atom or a $C_2$-$C_5$ aliphatic acyl group.

2. An oside compound according to claim 1, wherein X is the sulfur atom.

3. An oside compound according to claim 1, wherein Y is CH₃CO.

4. A therapeutic composition containing, in association with a physiologically acceptable excipient, at least one oside compound according to any one of claims 1 to 3.

5. A method of treatment of disorders of the venous circulation comprising administering to a patient, in need of such a treatment, an antithrombotic effective amount of an oside compound of the formula I according to claim 1.

6. An oside compound according to claim 1, wherein the sulfonylphenyl-β-D-thioxyloside is 4-(methylsulfonyl)phenyl 1,5-dithio-β-D-xylopyranoside.

7. An oside compound according to claim 1, wherein the sulfonylphenyl-β-D-thioxyloside is 4-[(4-fluorophenyl)sulfonyl]phenyl 1,5-dithio-β-D-xylopyranoside.

8. An oside compound according to claim 1, wherein the sulfonylphenyl-β-D-thioxyloside is 4-[(4-cyanophenyl)sulfonyl]phenyl 1,5-dithio-β-D-xylopyranoside.

* * * * *

UNITED STATES PATENT AND TRADEMARK OFFICE
CERTIFICATE OF CORRECTION

PATENT NO. : 5,100,913
DATED : March 31, 1992
INVENTOR(S) : Soth Samreth et al

It is certified that error appears in the above-indentified patent and that said Letters Patent is hereby corrected as shown below:

On the title page, Formula I in the Abstract; formula I on column 1; formula III, IV and V on column 2; formula I on column 12 (table I); and the formula I on column 13 (table II and claim 1); change the 7-membered formula to

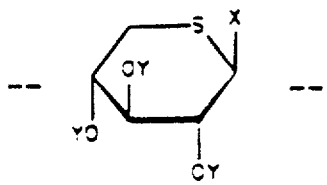

Signed and Sealed this

First Day of February, 1994

Attest:

BRUCE LEHMAN

Attesting Officer

Commissioner of Patents and Trademarks